(12) United States Patent
Bigazzi et al.

(10) Patent No.: US 8,632,541 B2
(45) Date of Patent: Jan. 21, 2014

(54) SELF-CENTRING ELBOW FIXATION DEVICE WITHOUT GUIDE WIRE

(76) Inventors: Prospero Bigazzi, Florence (IT); Andrea Corvi, Florence (IT)

( * ) Notice: Subject to any disclaimer, the term of this patent is extended or adjusted under 35 U.S.C. 154(b) by 756 days.

(21) Appl. No.: 12/668,103

(22) PCT Filed: Jul. 3, 2008

(86) PCT No.: PCT/IT2008/000447
§ 371 (c)(1),
(2), (4) Date: May 5, 2010

(87) PCT Pub. No.: WO2009/008023
PCT Pub. Date: Jan. 15, 2009

(65) Prior Publication Data
US 2010/0249778 A1    Sep. 30, 2010

(30) Foreign Application Priority Data
Jul. 11, 2007 (IT) .................. FI2007A0157

(51) Int. Cl.
*A61F 5/04* (2006.01)
(52) U.S. Cl.
USPC .................................. 606/54; 606/53; 602/16

(58) Field of Classification Search
USPC ............... 606/53–59; 602/5, 16, 20; 403/113, 403/116, 117
See application file for complete search history.

(56) References Cited

U.S. PATENT DOCUMENTS
6,152,925 A * 11/2000 Marsh et al. .................... 606/54

FOREIGN PATENT DOCUMENTS
WO    WO 99/29247    6/1999
WO    WO 99/04549    9/1999

* cited by examiner

*Primary Examiner* — Jerry Cumberledge
*Assistant Examiner* — Nicholas Plionis
(74) *Attorney, Agent, or Firm* — McGlew and Tuttle, P.C.

(57) ABSTRACT

A first arched slot or slit connection element (15) and a second linear slot or slit connection element (19, 21) are provided for cursors (13, 30) which can slide and be locked along said slots or slits; the connection element engaged with the humeral stem is self-centring and is provided with a hinge (32, 34) defining the articulation axis of the elbow, when—after repeated flexion-extension—said cursor is no longer subject to significant movements.

16 Claims, 7 Drawing Sheets

SELF-CENTRING ELBOW FIXATION DEVICE WITHOUT GUIDE WIRE

In the post-operative treatment of rigidities or capsuloligamentous lesions of the elbow, use of the dynamic external fixation device is very important as it permits immediate mobilisation, protecting the ligamentous reconstruction from varus-valgus stress and, where indicated, avoiding contact of the articular surfaces in order to obtain healing of the ligaments, fundamental for stability.

Fitting of the current external fixation devices comprises a very delicate step consisting in the temporary positioning of a supracondylar guide wire along the axis of the centre of rotation of the elbow, which is an invasive operation not without drawbacks. This operation, in fact, not only causes a further trauma of the articulation which must be exposed, but also prolongs the duration of the operation, exposes operators and patient to a considerable amount of radiation (the procedure is performed under radioscopic control) and also involves the risk of lesion of the ulnar nerve (fundamental for correct functioning of the hand), and also incorrect assembly of the fixation device, not always perfectly in line with the centre of rotation of the elbow.

The subject of the present invention is a fixation device, which self-aligns with the centre of rotation of the joint and then maintains said alignment in a stable manner, avoiding the use of supracondylar guide wire (Kirschner wire).

The elbow fixation device in question—involving humeral fiches and ulnar fiches suitable for engaging a humeral stem and an ulnar stem—more particularly can comprise a first arched slot or slit connection element and a second linear slot or slit connection element for respective sliding cursors which can be locked along said slots or slits; one of said connection elements is engaged in the humeral stem and the other is engaged in the ulnar stem; one of said cursors is characteristically self-centring and is provided with a hinge defining the articulation axis of the elbow; this cursor can be positioned and locked in place, where it is not subject to significant movements due to repeated flexion and extension.

In a possible embodiment, the elbow fixation device in question—involving humeral fiches and ulnar fiches suitable for engaging the humeral stem and ulnar stem—comprises:
  in a housing, a first arched slot or slit connection for the humeral stem with respective locking means, and a second linear slot or slit connection; a sliding cursor which can be locked along said second linear slit connection;
  a coupling element between the ulnar stem and said cursor, so that said cursor can be moved along said second linear connection due to flexion and extension movements of the limb; and
  on said cursor a hinge suitable for defining the articulation axis of the elbow when the cursor is in a position in which it is not subject to movements along said linear slot or slit due to flexion and extension and is therefore locked in said position.

Said angular connection for the humeral stem can feature in said housing a double arched slot or slit with centre coinciding with the angular connection of the humeral stem; the locking means of the humeral stem can be operated along said double arched slot or slit to lock the humeral stem in several angular positions along said double arched slot or slit as far as a position in which no movements of the hinge along the linear slot or slit connection—due to flexion-extension of the limb—are observed, where the cursor can therefore be locked.

Said connection element between the ulnar stem and the cursor can be combined with a displacement mechanism.

Elements to protect against the penetration of dirt and other into the housing can be advantageously provided at the level of the slots.

The invention will be better understood by following the description and accompanying drawing, which shows a practical non-limiting example of the invention. In the drawing.

Figure 7:
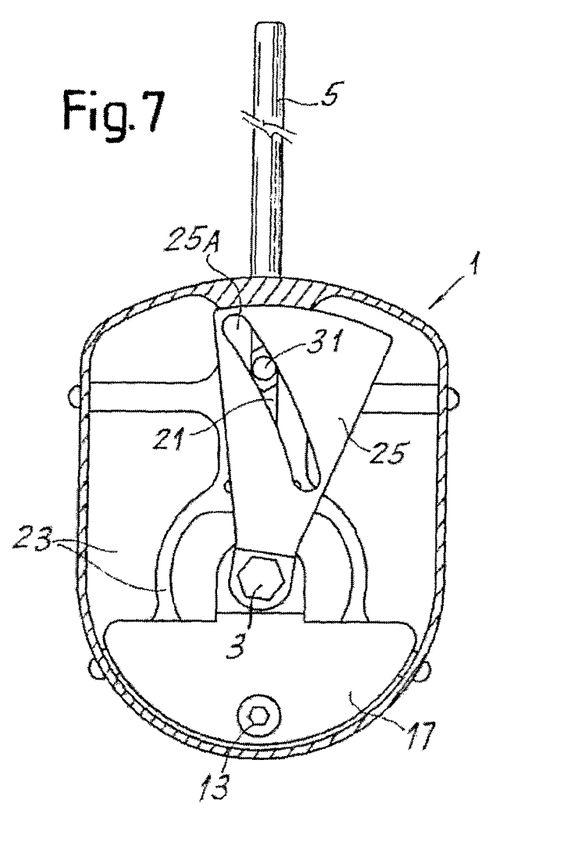
FIGS. 7 and 8 are two sections according to VII-VII and VIII-VIII of FIG. 2, enlarged.
Figure 8:
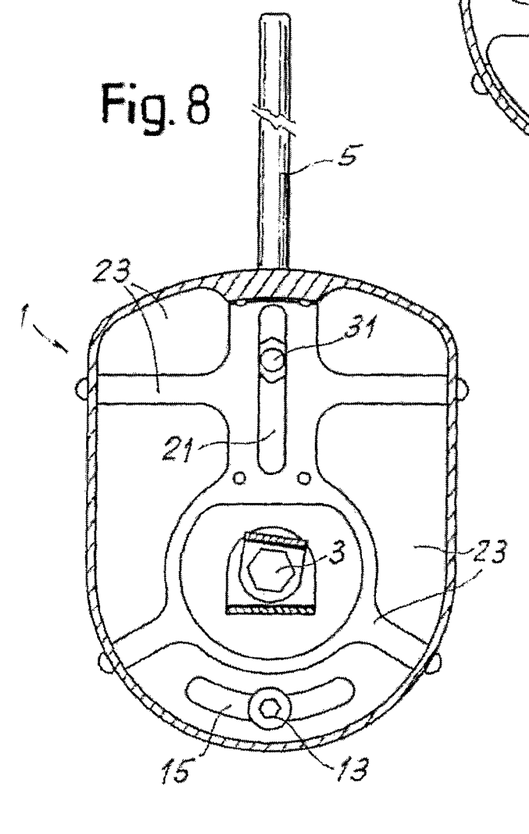
Figure 9:
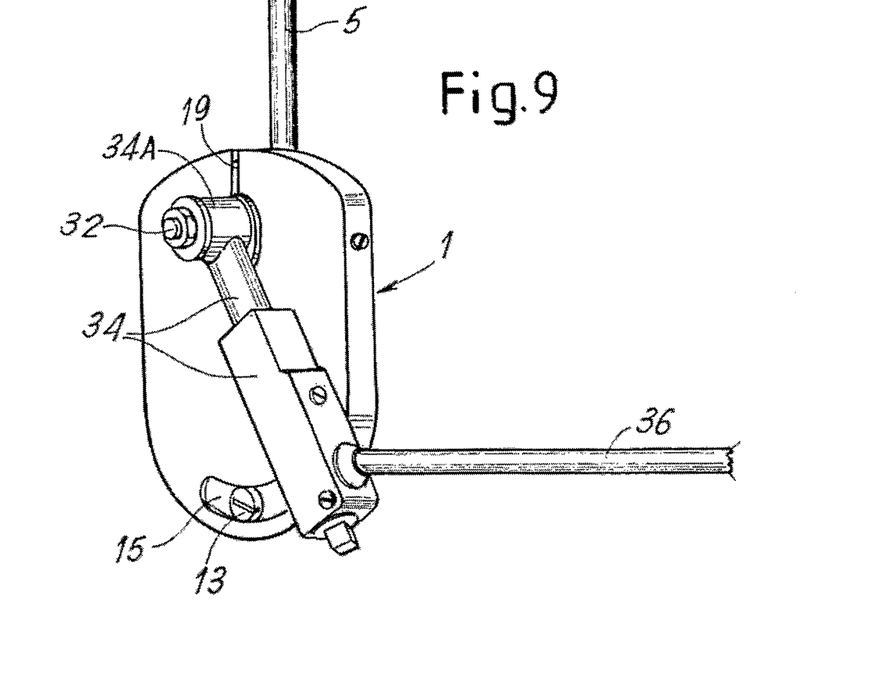
FIGS. 9 and 10 are two overall perspective views of the fixation device in question.
Figure 10:
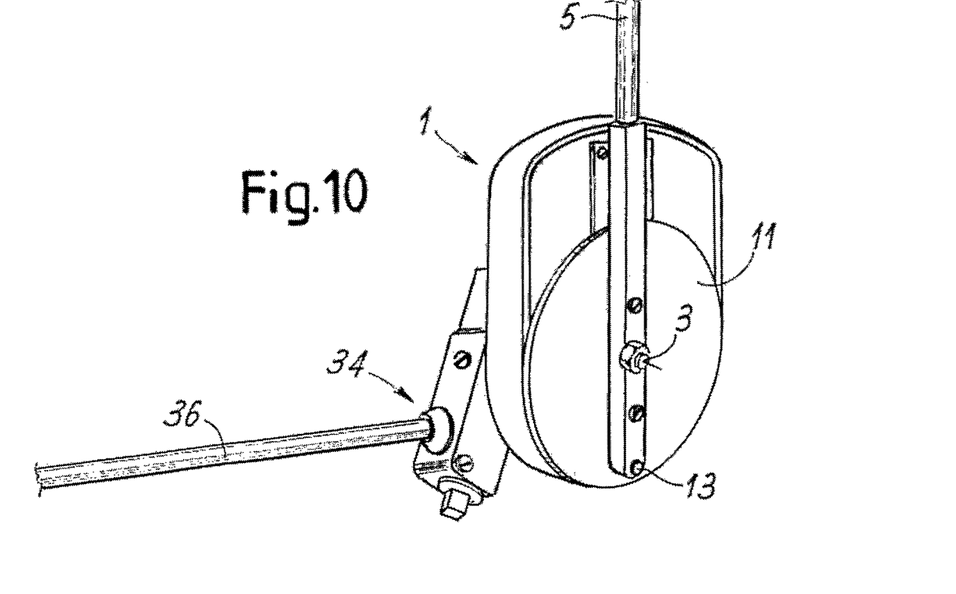
Figure 11:
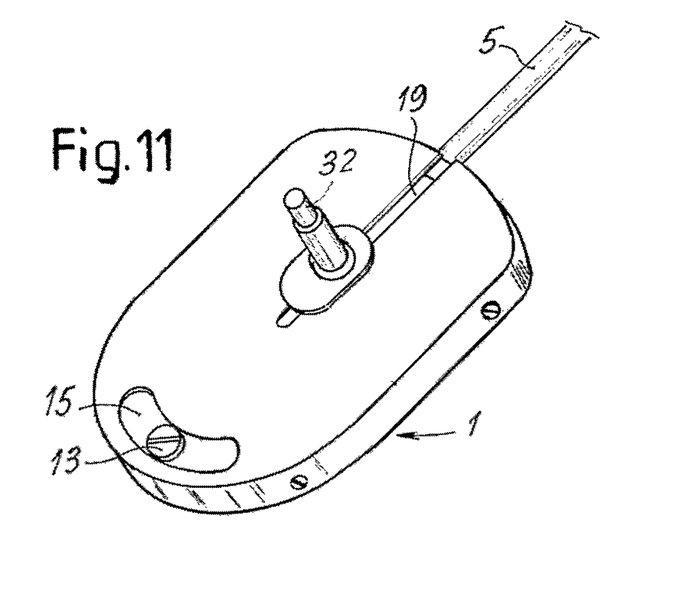
FIGS. 11 and 12 are two perspective details of a housing for the parts of the fixation device.
Figure 12:
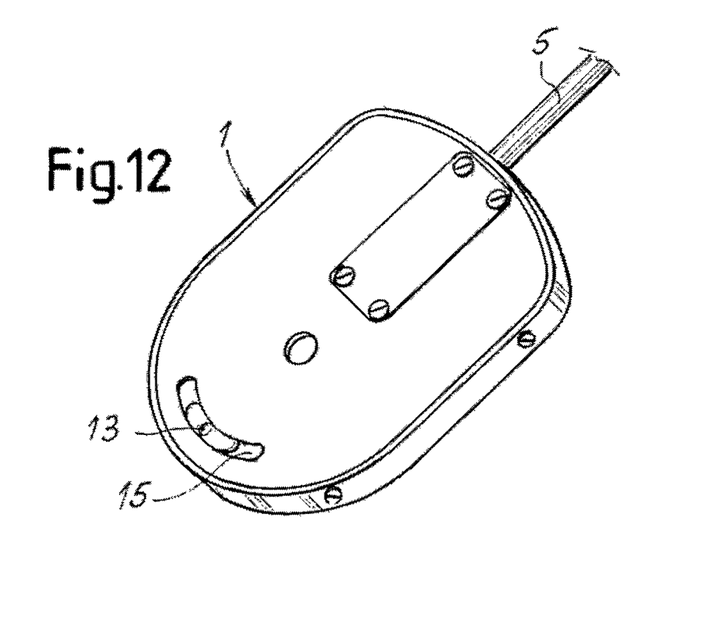
Figure 13:
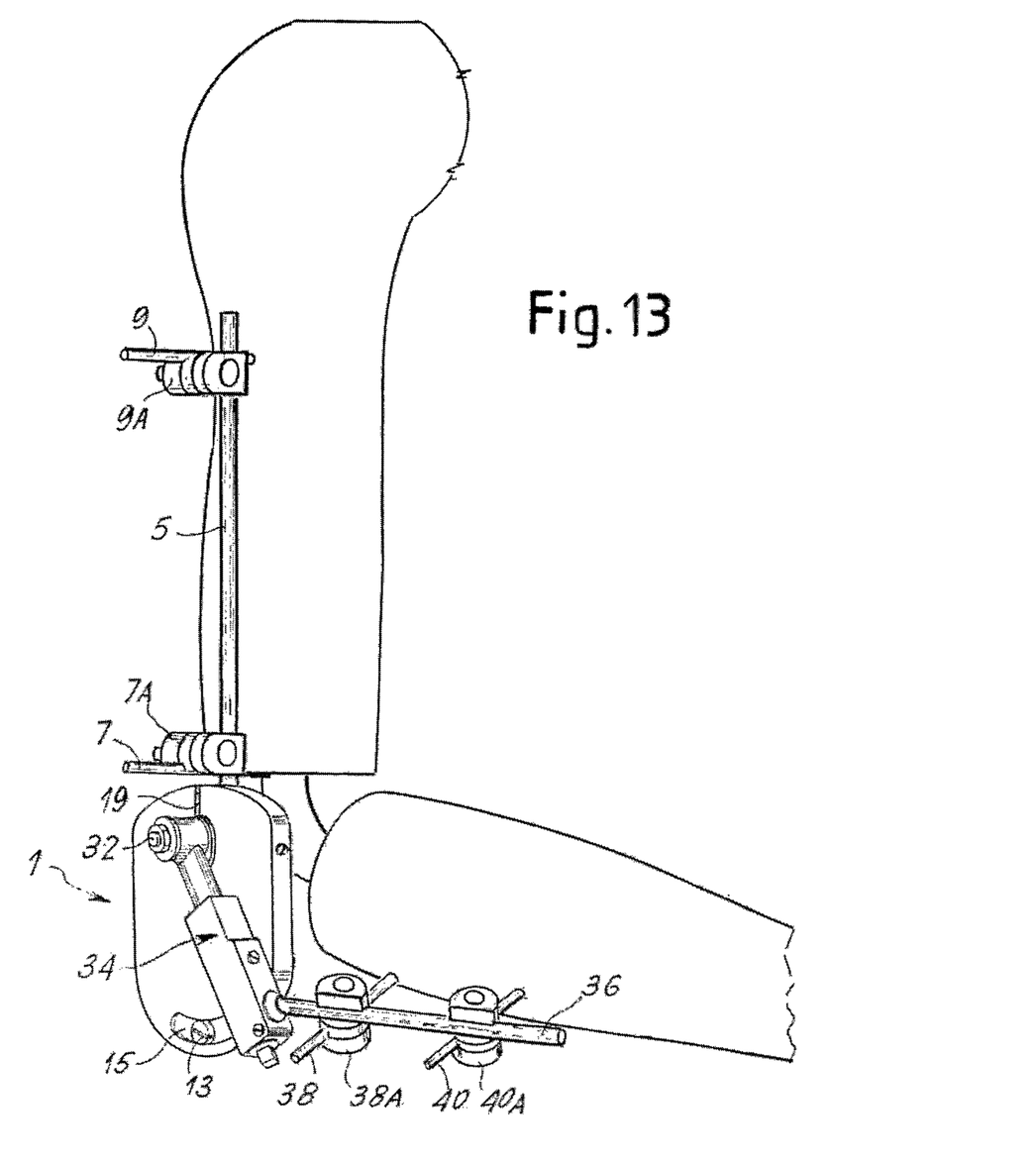
FIG. 13 is an overall perspective view of the fixation device applied.

In the drawing, 1 generically indicates a housing, the main part of the device. At the rear of said housing, the humeral support stem 5, which is applied to the humerus by means of two fiches 7 and 9 and relative clamps 7A and 9A, is jointed at 3; a disc-shaped covering and protection plate 11 is integral with the stem 5. At the end, the stem 5 houses a locking screw 13 which corresponds to a double arched slot 15 at the front and rear of the housing, with centre on the axis of the joint 3; a protective covering 17 is combined with the screw 13 (FIG. 7). At the front, the housing 1 also features a linear slot or slit 19 to be positioned roughly corresponding to the humeral stem 5; a slot or slit 21 obtained (FIG. 8) in a plate 23 inside the housing 1 corresponds to said slot 19. Between said plate 23 and the front wall of the housing 1 is a laminar protection element 25 (FIG. 7), jointed at 3 and with an arched and inclined slit 25A; this laminar element 25 constitutes a protection for the slots or slits 21 and 19, which therefore remain exposed only for a limited variable section along their extension.

Figure 1:
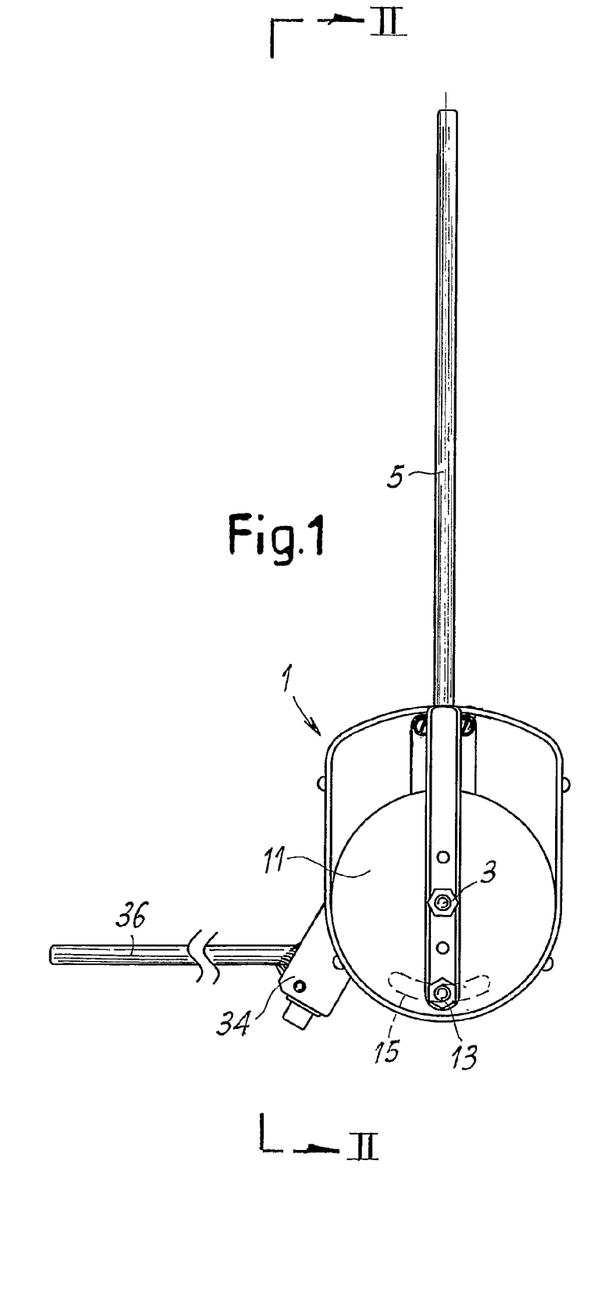
FIGS. 1, 2, 3 are three external views according to I-I of FIG. 2, II-II of FIG. 1 and III-III of FIG. 2.
Figure 2:
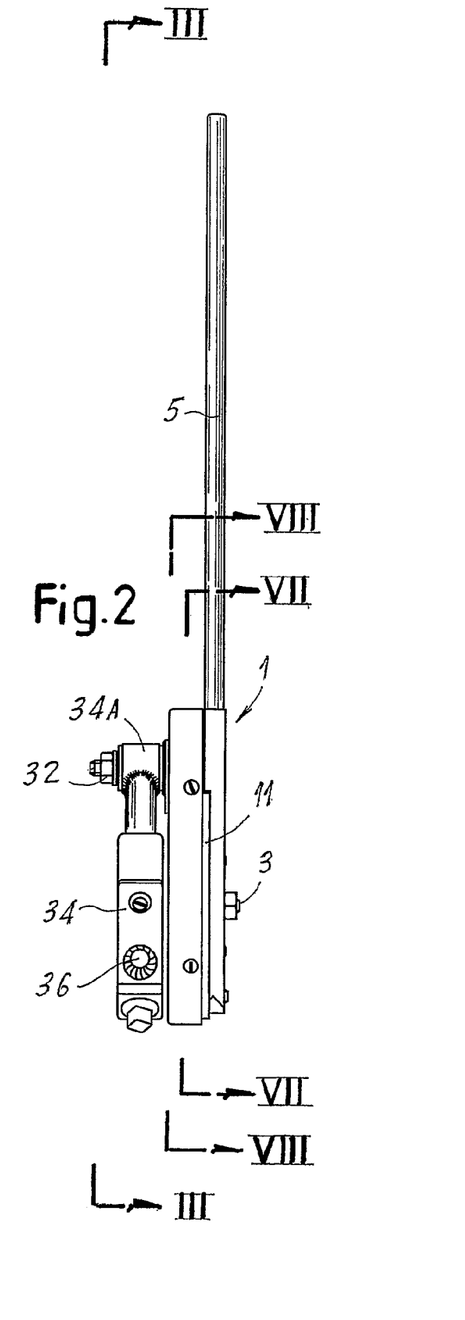
Figure 3:
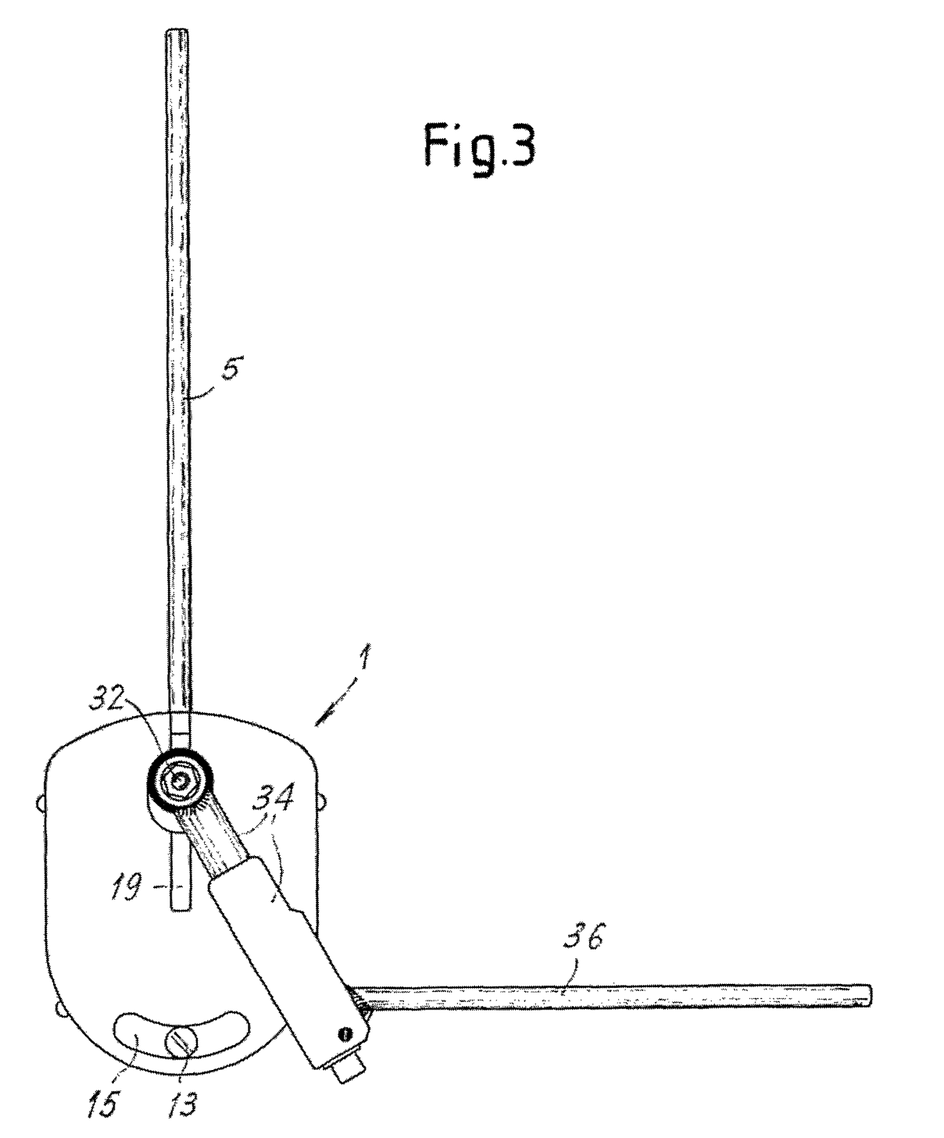
Figure 4:
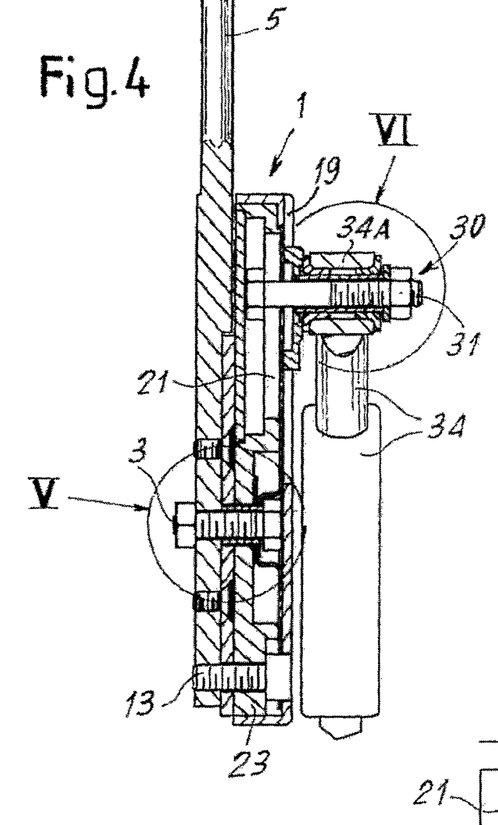
FIGS. 4, 5 and 6 are a section according to IV-IV of FIG. 3 and two enlarged details of the areas indicated by the arrows V and VI of FIG. 4.
Figure 5:
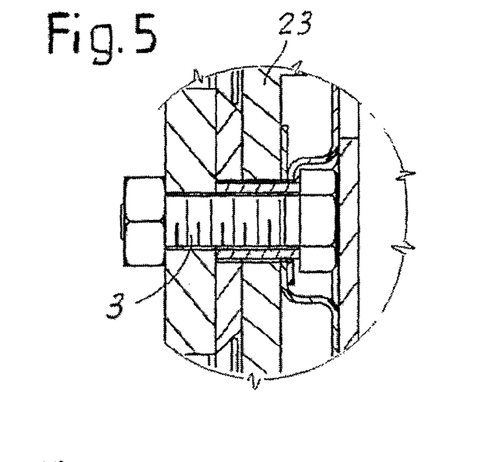
Figure 6:
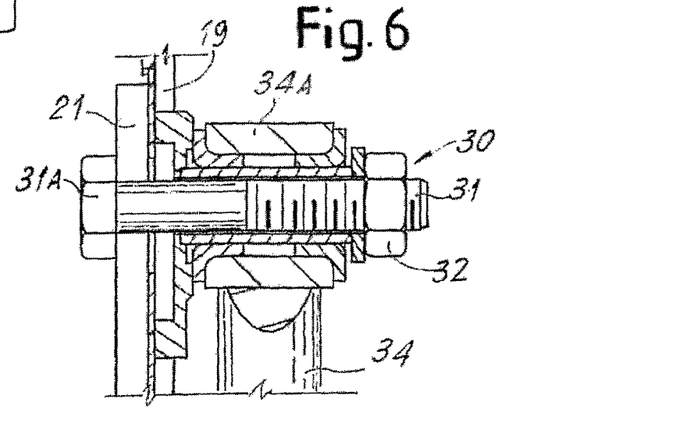

At the level of the slits 19 and 21 is a cursor generically indicated by 30, which runs along said two slits 19 and 21. This cursor 30 comprises (see in particular FIGS. 4 and 6) a screw pin 31 with the head 31A inside and the threaded end outside where a tightening nut 32 is engaged; the cursor 30 can be locked by means of nut 32 along the slit 21 in a specific position—when identified as described below—in which the axis of the pin 31 corresponds to the geometric axis of the natural ulnohumeral articulation of the elbow.

Around the pin 31 of the cursor 30 a hinge seat is provided—coaxial with the pin itself—for the terminal eyelet 34A of an element 34 connecting said cursor 30 and the ulnar stem 36; said stem 36 will be engaged in the forearm of the patient by means of clamps 38A and 40A engaged in fiches 38 and 40 for anchoring to the ulna and forearm. The connection element 34 can comprise a so-called "displacer" which increases the articular space between humerus and ulna by moving the ulnar component away from the centre of rotation.

From the above description it is clear that, having installed the elbow fixation device on the humerus and on the ulna, by flexing and extending the limb, the cursor 30 can be moved along the slits 19 and 21 (substantially parallel to the humerus) to a greater or lesser extent according to whether the cursor 30 is farther from or nearer to the instantaneous axis of rotation of the natural articulation of the elbow; only when this natural axis coincides with the axis of the pin 31 does the cursor not move; in this last condition the cursor 30 can be locked in position along the slits 19 and 21 by means of the nut 32.

In operational terms, the stem 5 must be provisionally locked by means of the screw 13 along the arched slots or slits 15 and the stem 36 must be provisionally locked by means of the screw 31, 32 along the linear slit 21 in an intermediate position by approximately positioning the screw 32 on the axis of the supracondylar elbow. The stems 5 and 36 are then engaged on the humerus and ulna, with the fiches 7, 9 and 38, 40 and the respective clamps 7A, 9A and 38A, 40A. At this point the screws 13 and 32 are loosened and the limb is flexed and extended; in this way any possible movements of the components 30 and 13 can be checked. After a few attempts, the angular position of the screw 13 along the slots or slits 15, in which the cursor 30 does not move during flexion and extension, is identified. At this point the stem 5 is locked permanently by means of the screw 13 in the above-mentioned angular position along the arched slits 15, and the cursor 30 is locked permanently along the slots or slits 19, 21 in the longitudinal position reached by it. The axis of the pin 31 coincides with the best approximation of the instantaneous axis of rotation of the elbow, i.e. practically with the axis of the articulation.

The elbow fixation device thus functions without recourse to the invasive and hazardous insertion of a supracondylar guide wire.

The various protections 11, 17, 25 provide long-term protection of the device from penetration of dust and foreign bodies.

The fixation device described above can be provided with further accessories, including:
- a system for restricting the movement arc to a certain number of degrees;
- a system for application to the fixation device and suitable, by means of a preloaded spring system, for performing a constant and progressive extension thrust;
- a system analogous to the previous one, to perform a flexion thrust.

It is understood that the drawing only shows an example provided solely as a practical demonstration of the invention, it being possible to vary the forms and arrangements of said invention without departing from the scope of the concept underlying said invention. Any reference numbers in the attached claims are designed to facilitate reading of the claims with reference to the description and the drawing, and do not limit the scope of the protection represented by the claims.

The invention claimed is:

1. An elbow fixation device comprising:
    a humeral stem;
    an ulnar stem;
    humeral fiches engaging said humeral stem;
    ulnar fiches engaging said ulnar stem; and
    a housing with a first arched slot connection with a first cursor and a second linear slot connection with a second cursor, said first cursor and said second cursor being slidable and lockable along said slot connections, said first arched slot connection and said second linear slot connection with respective cursors being arranged in said housing, one of said slot connections being engaged with said humeral stem and the other of said slot connections being engaged with said ulnar stem, said second cursor including a hinge defining an articulation axis of the ulnar stem relative to the humeral stem, said second cursor being self-centering with respect to an elbow articulation axis prior to locking thereof, whereby, after self-centering, the second cursor is locked.

2. An elbow fixation device according to claim 1, wherein:
    said first arched slot connection is engaged with said humeral stem; and
    said second linear slot connection is engaged with said ulnar stem.

3. An elbow fixation device according to claim 2, further comprising:
    a coupling element between said ulnar stem and said second cursor, whereby, prior to locking, said second cursor is moveable along said second linear slot connection due to flexion and extension of a limb of the elbow.

4. An elbow fixation device according to in claim 3, wherein:
    said arched slot connection engaged with said humeral stem is a double arched slot with a center coinciding with an angular connection of said humeral stem to said housing;
    said first cursor operates along said double arched slot to lock said humeral stem in one of several angular positions along said double arched slot; and
    the one of several angular positions, following flexion-extension of the limb, allows no observed movements of the hinge along the linear slot connection, where the second cursor can therefore be locked.

5. An elbow fixation device according to claim 4, further comprising two laminar protection elements protecting said double arched slot.

6. An elbow fixation device according to claim 3, wherein said coupling element between the ulnar stem and said second cursor is a displacer.

7. An elbow fixation device according to claim 3, further comprising protection elements connected to said housing to protect against the penetration of dirt and other debris inside said housing at a level of slots of said slot connections.

8. An elbow fixation device according to claim 3, wherein a laminar protection element with a slit is jointed to the housing to protect a linear slot of said linear slot connection.

9. An elbow fixation device comprising:
    a housing defining an arched slot and a linear slot;
    an arched slot adjustment and locking connection comprising the arched slot and a first cursor engaging the arched slot, the first cursor being slidable and lockable along the arched slot;
    a linear slot adjustment and locking connection comprising the linear slot and a second cursor engaging the linear slot, the second cursor being slidable and lockable along the linear slot, the second cursor further comprising a hinge;
    a humeral stem connected to one of the first cursor and the second cursor;
    an ulnar stem connected to another of the first cursor and the second cursor;
    humeral fiches connected to the humeral stem; and
    ulnar fiches connected to the ulnar stem, wherein:
    the hinge is connected to one of the humeral stem and the ulnar stem to define an articulation axis of the ulnar stem relative to the humeral stem; and
    the second cursor is lockable relative to the linear slot, and, prior to locking, the second cursor is self-positioning along the linear slot with respect to an elbow axis during repeated articulation of the elbow, and whereby after self-positioning, the second cursor is locked.

10. An elbow fixation device according to claim 9, wherein:
    the arched slot connection adjusts a position of the humeral stem relative to the housing; and the linear slot connection adjusts a position of the ulnar stem relative to the housing.

11. An elbow fixation device according to claim 10, further comprising:
a coupling element between the ulnar stem and the second cursor, the coupling element providing movement of the ulnar stem toward and away from a center of rotation of the hinge.

12. An elbow fixation device according to claim 11, wherein the coupling element between the ulnar stem and the second cursor is a displacer.

13. An elbow fixation device according to claim 11, further comprising protection elements connected to the housing to protect against the penetration of dirt and other debris inside the housing at a level of slots of the slot connections.

14. An elbow fixation device according to in claim 10, wherein:
the arched slot connection engaged with the humeral stem is a double arched slot with a center coinciding with an angular connection of the humeral stem to the housing;
the first cursor operates along the double arched slot to lock the humeral stem in one of several angular positions along the double arched slot; and
the one of several angular positions, following flexion-extension of the limb, allows no observed movements of the hinge along the linear slot connection, where the second cursor can therefore be locked.

15. An elbow fixation device according to claim 14, further comprising two laminar protection elements protecting the double arched slot.

16. An elbow fixation device according to claim 9, wherein a laminar protection element with a slit is jointed to the housing to protect the linear slot.

* * * * *